United States Patent
Erdogan

(10) Patent No.: US 10,702,373 B2
(45) Date of Patent: Jul. 7, 2020

(54) HAIR GRAFT PLACEMENT APPARATUS USED FOR HAIR TRANSPLANTATIONS

(71) Applicant: ASMED OZEL SAC EKIMI SAGLIK HIZMETLERI TICARET A.S, Atesehir-Istanbul (TR)

(72) Inventor: Koray Erdogan, Atasehir/Istanbul (TR)

(73) Assignee: ASMED OZEL SAC EKIMI SAGLIK HIZMETLERI TICARET A.S, Atasehir-Istanbul (TR)

( * ) Notice: Subject to any disclaimer, the term of this patent is extended or adjusted under 35 U.S.C. 154(b) by 0 days.

(21) Appl. No.: 16/347,479

(22) PCT Filed: Jan. 10, 2017

(86) PCT No.: PCT/TR2017/050011
§ 371 (c)(1),
(2) Date: May 3, 2019

(87) PCT Pub. No.: WO2018/084818
PCT Pub. Date: May 11, 2018

(65) Prior Publication Data
US 2019/0282357 A1  Sep. 19, 2019

(30) Foreign Application Priority Data
Nov. 5, 2016 (TR) .............................. u 2016/10548

(51) Int. Cl.
| | | |
|---|---|---|
| *A61F 2/10* | (2006.01) |
| *A61B 17/34* | (2006.01) |
| *A61B 17/3205* | (2006.01) |
| *A61B 17/00* | (2006.01) |

(52) U.S. Cl.
CPC .......... *A61F 2/10* (2013.01); *A61B 17/32053* (2013.01); *A61B 17/3468* (2013.01); *A61B 2017/00424* (2013.01); *A61B 2017/00438* (2013.01); *A61B 2017/00752* (2013.01)

(58) Field of Classification Search
CPC .................... A61F 2/10; A61N 5/0617; A61B 2018/00476
USPC ........................................ 623/11.11; 606/133
See application file for complete search history.

(56) References Cited

U.S. PATENT DOCUMENTS

| | | | | |
|---|---|---|---|---|
| 2004/0039400 | A1 | 2/2004 | Schmieding | |
| 2010/0298837 | A1* | 11/2010 | Gorensek | A61F 2/4611 606/99 |
| 2013/0006143 | A1* | 1/2013 | Neoh | A61B 10/0275 600/567 |
| 2015/0081017 | A1* | 3/2015 | Abbate | A61K 9/70 623/10 |
| 2016/0120574 | A1* | 5/2016 | Shiao | A61B 17/3468 606/187 |

(Continued)

FOREIGN PATENT DOCUMENTS

WO  WO 03/096906 A2  11/2003

*Primary Examiner* — Suzette J Gherbi
(74) *Attorney, Agent, or Firm* — John Alumit

(57) ABSTRACT

Hair Graft Placement Apparatus Used for Hair Transplantation. This invention is related to a hair graft placement apparatus that enables the placement of previously obtained hair grafts into incisions made on a bald scalp during the hair transplantation process. The invention consists of wall thickness (1), end region (2), narrow channel (3), wide channel (4), metal tube (5), handle grip (6) and finger slot (7).

5 Claims, 2 Drawing Sheets

(56) References Cited

U.S. PATENT DOCUMENTS

Figure 1:
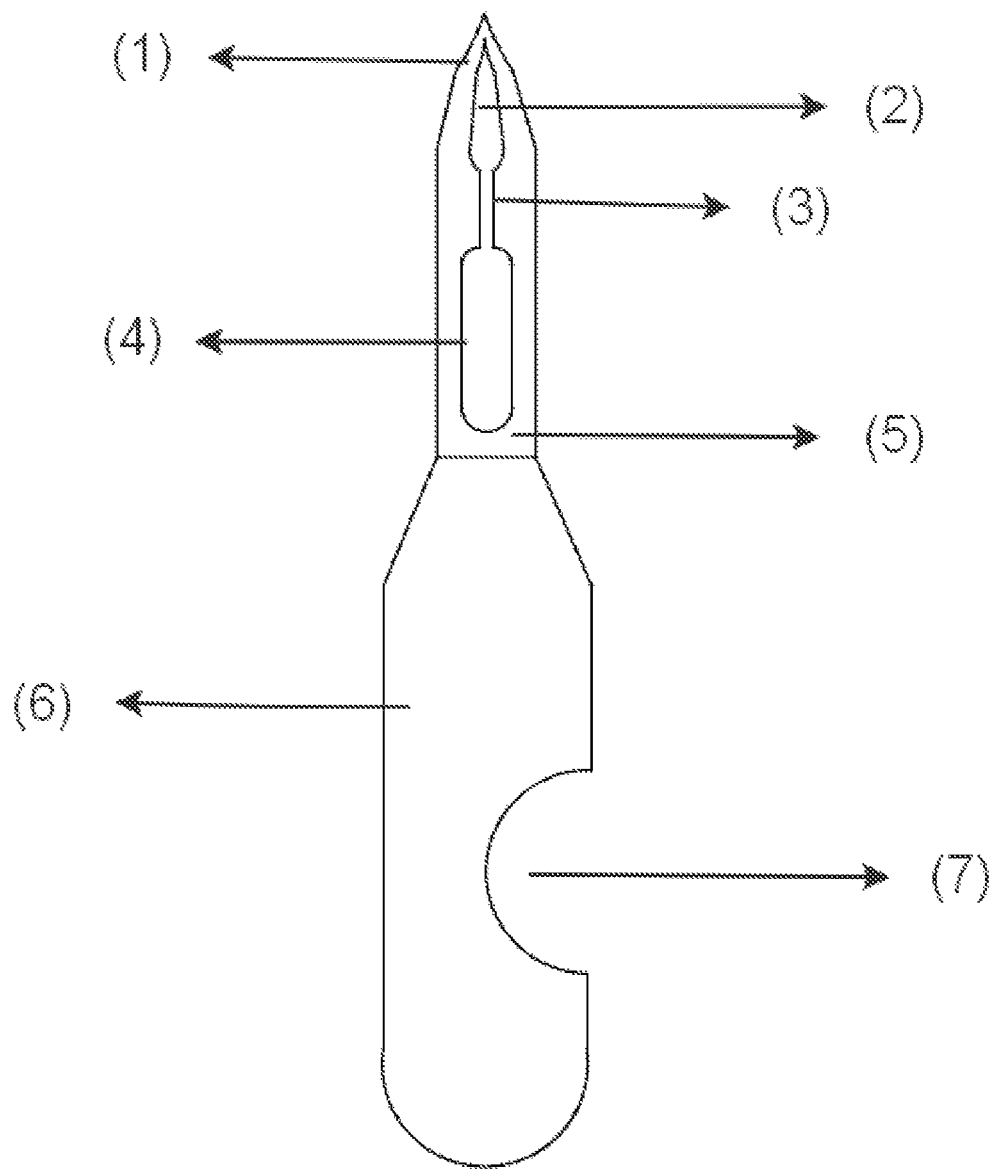

| | | | |
|---|---|---|---|
| 2017/0027659 A1* | 2/2017 | Goddard | A61B 90/08 |
| 2017/0087310 A1* | 3/2017 | Clement | A61M 13/003 |
| 2017/0265896 A1* | 9/2017 | Keren | A61F 2/10 |
| 2019/0090869 A1* | 3/2019 | Keating | A61B 17/0401 |
| 2019/0117378 A1* | 4/2019 | Loria | A41G 5/0053 |

* cited by examiner

HAIR GRAFT PLACEMENT APPARATUS USED FOR HAIR TRANSPLANTATIONS

TECHNICAL FIELD

This invention is related to a hair graft placement apparatus that enables the placement of previously obtained hair grafts into incisions made on the bald scalp during the hair transplantation process.

KNOWN STATUS OF THE TECHNIQUE

During embryogenesis, so-called "hairs" (non-living extensions) develop from the follicles that originate from the elongation of the mesenchyme cells in the direction of the dermis or subcutaneous tissue. The human body contains hairs of different lengths in many areas.

Invisible hair follicle pockets are present in the head area of the human body, in the skin area that is called the scalp. The follicles become active via signals from certain body areas and hair emerges from underneath the scalp growing an average of 0.41 mm per day. Typically, the human head area contains 100.000-125.000 hair fibres. Each hair fibre has its own life cycle independent from the others. Each day, during the course of this cycle, an average of 100 hair fibres are lost.

In addition to the normal hair loss pattern, people who are exposed to conditions such as stress, smoking, radiation, chemotherapy, various medical treatments, genetic character etc. experience even more hair loss. However, they do not observe any hair regrowth. With time, some parts of the scalp or all of it may become bald. The FUE (Follicular Unit Extraction) hair transplantation method enables the harvesting of hair follicles and their subsequent transplantation to other bald scalp areas thus providing hair coverage where it was previously lacking.

Hair transplantation typically begins with the shaving of the patient's entire scalp area. The hair follicles are then extracted from the patient's subcutaneous scalp tissue using either a manual surgical punch or motorized device. After extraction, pre-made incisions are performed using micro sapphire blades in the area of the scalp where the grafts are to be transplanted. Grafts are traditionally inserted with a slight pushing motion into the pre-made incisions using forceps. The viability of the grafts using this placement method is 8 out of 10 grafts. Therefore, a loss of 20% is present. Since this procedure is being performed over a long period of time, it can be tedious and costly. An inefficiency rate of 20% could be considered high in this case. Additionally, the expected density and natural appearance desired can be affected which in turn, affects potential outcomes. With this system, transplantation incisions take longer to heal and anticipated hair growth can take up to 1 year.

THE PROBLEMS THIS INVENTION AIMS TO SOLVE AND ANALYSIS

This invention enables the uncomplicated placement of grafts into pre-made incisions with 100% efficiency during the hair transplantation procedure, and enables faster growth thereafter.

Prior to the conception of this new instrument, the placement of hair grafts into pre-made incisions using forceps was considered the norm. However, the use of forceps left room for error in the placement and embedding of the graft. This was due to technician fatigue and the resulting inappropriate pressure put on the forceps, the restriction of the incision size while awaiting receipt of the graft, and the inability to determine the angle of the incision. Often times, under these conditions, grafts began to curl within the incision site in a period of less than 24 hours. This phenomenon, in turn, inhibited hair growth and expected outcomes thereby affecting the healthy growth of 2 out of 10 hair grafts. As a hypothesis, in procedure being performed with a graft count of at least 2000-2500 grafts where forceps are used for implantation, one can expect a loss of 500 grafts. This situation is compounded by a failure to reach the expected density and the natural look desired.

Since the wall thickness of the instrument is 0.05 mm, it is possible to insert the graft into the incision without pressure and without searching for incision angles. This avoids curling and affords greater growth rates with 100% success. The 100% success rate and avoidance of tedious and costly hair transplantation procedures while reaching the expected density and natural appearance is an ideal result.

The instrument is equally effective for long hair or partially shaven FUE procedures. In long hair or partially shaven FUE, the patient's hair is shortened or partially shaven for the extraction of the follicles. The grafts are placed into pre-made micro incisions as in fully shaven FUE procedures. (The incisions afterwards appear as thousands of small, red points with the naked eye). Following the implantation of the grafts, it takes approximately 12 months for this appearance to completely disappear. With these two FUE procedures, incision sites are covered by long hair and can barely be seen through the hair fibers. Thanks to this possibility, patients are able to resume their normal lives the following day.

DEFINITION OF THE INVENTION BY PICTURES

Figure 2:
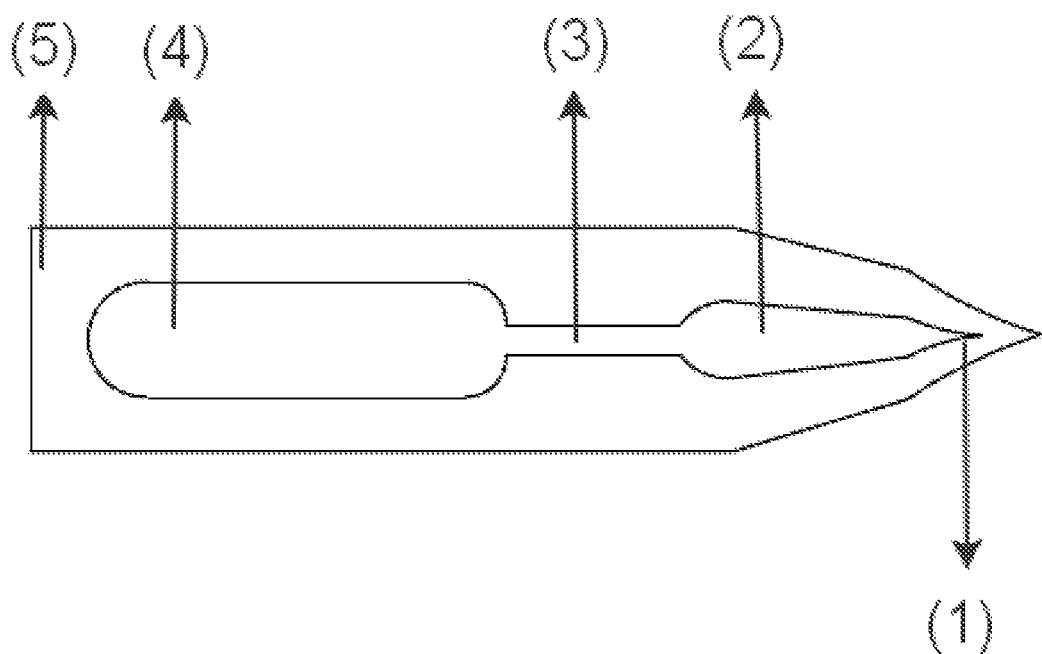

FIG. 1 Side view of the Invention
FIG. 2 End Region View of the Invention

SECTION NUMBERS

1. Wall thickness
2. End Region
3. Narrow canal
4. Wide canal
5. Metal tube
6. Handle grip
7. Finger slot

TECHNICAL CHARACTERISTICS OF THE INVENTION AND EXPLANATIONS

This invention is related to a hair graft placement apparatus that enables the placement of previously obtained hair grafts into micro incisions performed on a bald scalp during the hair transplantation process. The invention consists of wall thickness (1), end region (2), narrow canal (3), wide canal (4), metal tube (5), handle grip (6) and finger slot (7).

The hair transplantation begins with the extraction of hair follicles. During the extraction of the hair follicles, shaving or non-shaving of the hair is not important in terms of the application. The invention is also suited for the transplantation of long hair. The extracted hair grafts are held in a suitable environment and micro incisions are made with sapphire blades in the area of implantation.

The person that is performing the hair transplantation procedure places his/her finger of the right or left hand into the finger slot (7) and holds the invention via the handle grip (6). The previously extracted hair grafts that are awaiting transplant are positioned into the narrow incision (3) via forceps under a microscope that enables the placement of the hair follicle into the incision (4). The narrow channel (3), wide channel (4) are located inside the metal tube (5). The wall thickness (1) present in the end region (2) was designed to be 0.05 mm thick that enables easy insertion and extraction within the incisions.

The operator places the hair follicle into the invention and places the end region (2) into the incision. The hair graft within the narrow channel (3) and wide channel (4) is slid within the channel with the help of a thin slider. No pressure is exerted on the hair graft during this procedure that may cause any harm to the hair graft. The hair graft moves without sticking at any point, and therefore does not sustain any harm and does not curl up. After the graft reaches the necessary depth within the metal tube (5), the placement tool is retracted and the hair follicle is left within the incision. The rate of success via this invention technique is 100%.

The handle grip (6) consists of silicone and prevents slippage. Additionally, it suitable for cleaning in high temperature devices used for sterilization.

A finger slot (7) is present where the operator can position his/her finger on the placement tool. The operator is able to easily perform the required movements via the finger slot (7). The finger slot (7) may be located on the right or left edges of the placement tool.

The invention claimed is:

1. A hair graft placement apparatus for placing a hair graft into an incision made on a bald scalp by a user having a finger, the apparatus comprising:
    a forceps portion having a wall thickness, an end region, a narrow channel adjacent, a wide channel, and a metal tube;
    a handle portion having a handle grip and a finger slot;
    wherein the wall thickness is present at the end region of the forceps;
    wherein the narrow channel and the wide channel are located inside the metal tube;
    wherein the handle grip comprises silicon; and
    wherein the finger slot is located on the handle grip in a position proximal the user's finger when the user places the hair graft into the incision.

2. The apparatus of claim 1, wherein the end region comprises a wall thickness of 0.05 mm, thereby enabling entrance of the hair graft into the incision.

3. The apparatus of claim 1, wherein the narrow channel and the wide channel slide inside the metal tube while holding the hair graft.

4. The apparatus of claim 1, this invention wherein the finger slot is located on the right edge of the handle portion.

5. The apparatus of claim 1, wherein the finger slot is located on the left edge of the handle portion.

* * * * *